US00PP14288P29

(12) United States Plant Patent
Brown

(10) Patent No.: US PP14,288 P2
(45) Date of Patent: Nov. 11, 2003

(54) PETUNIA PLANT NAMED 'COBDARKINK'

(50) Latin Name: *Petunia×hybrida*
Varietal Denomination: Cobdarkink

(75) Inventor: Graham Noel Brown, Baulkham Hills (AU)

(73) Assignee: Nuflora International Pty. Ltd., Sydney (AU)

( * ) Notice: Subject to any disclaimer, the term of this patent is extended or adjusted under 35 U.S.C. 154(b) by 0 days.

(21) Appl. No.: 10/171,851

(22) Filed: Jun. 17, 2002

(51) Int. Cl.[7] ..... A01H 5/00
(52) U.S. Cl. ..... Plt./356
(58) Field of Search ..... Plt./356

*Primary Examiner*—Bruce R. Campell
*Assistant Examiner*—June Hwu
(74) *Attorney, Agent, or Firm*—C. A. Whealy

(57) ABSTRACT

A distinct cultivar of Petunia plant named 'Cobdarkink', characterized by its compact, uniform cascading and outwardly spreading plant habit; freely and continuous branching habit; and numerous double dark pink-colored flowers.

1 Drawing Sheet

Botanical classification/cultivar designation: Petunia×hybrida cultivar Cobdarkink.

BACKGROUND OF THE INVENTION

The present Invention relates to a new and distinct cultivar of Petunia plant, botanically known as Petunia×hybrida, and hereinafter referred to by the cultivar name Cobdarkink.

The new Petunia is a product of a planned breeding program conducted by the Inventor in Baulkham Hills, New South Wales, Australia. The objective of the breeding program is to create new Petunias with numerous double flowers with attractive flower colors.

The new Petunia originated from a cross made by the Inventor in 1998 of a proprietary Petunia selection identified as X96.410.1, not patented, as the female, or seed parent, with the Petunia cultivar Cobink, disclosed in U.S. Plant Pat. No. 12,012, as the male, or pollen parent. The new Petunia was selected as a single plant from the resulting progeny by the Inventor in October, 1999, in Cobbitty, New South Wales, Australia, on the basis of its dark pink double flowers.

Asexual reproduction of the new cultivar by terminal cuttings taken in Cobbitty, New South Wales, Australia since October, 1999 has shown that the unique features of this new Petunia are stable and reproduced true to type in successive generations.

SUMMARY OF THE INVENTION

Plants of the cultivar Cobdarkink have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Cobdarkink'. These characteristics in combination distinguish 'Cobdarkink' as a new and distinct cultivar:

1. Compact, uniform cascading and outwardly spreading plant habit.
2. Freely and continuous branching.
3. Numerous double flowers that are dark pink in color.

Plants of the new Petunia differ from plants of the female parent, the selection X96.410.1, primarily in flower color and flower form as plants of the female parent have white-colored single flowers.

Plants of the new Petunia differ from plants of the male parent, the cultivar Cobink, primarily in flower color as plants of the cultivar Cobink have lighter pink-colored flowers than plants of the new Petunia.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Petunia.

The photograph at the top of the sheet comprises a side perspective view of a typical flowering plant of 'Cobdarkink' grown in a 20-cm hanging basket container and was about 14 weeks old.

The photograph at the bottom of the sheet comprises a close-up view of a typical flower bud, a typical opening flower, upper and lower surfaces of typical fully opened flowers, and lower and upper surfaces of typical leaves of 'Cobdarkink'.

DETAILED BOTANICAL DESCRIPTION

The aforementioned photographs and following observations and measurements describe plants grown in Encinitas, Calif., in an outdoor nursery during the late winter and early spring with day temperatures about 24° C., night temperatures about 19° C., and light levels about 4,000 foot-candles. Plants were grown for 14 weeks in 20-cm containers with one plant per container and were pinched one time. Color references are made to The Royal Horticultural Society Colour Chart except where general terms of ordinary dictionary significance are used.

Botanical classification: Petunia×hybrida cultivar Cobdarkink.

Parentage:

*Female parent.*—Proprietary Petunia×hybrida selection identified as X96.410.1, not patented.

*Male parent.*—Petunia×hybrida cultivar Cobink, disclosed in U.S. Plant Pat. No. 12,012.

Propagation:

*Type cutting.*—Terminal vegetative cuttings.

*Time to initiate roots.*—About 10 days at 22° C.

*Time to develop roots.*—About 21 days at 22° C.

*Root description.*—Fine, fibrous, white in color.

*Rooting habit.*—Freely branching, dense.

Plant description:

*Form.*—Annual flowering plant; indeterminate; compact; initially upright, then cascading and outwardly spreading; uniform; plants eventually becoming hemispherical to spherical in shape. Viscid and glandular pubescent. Freely basal branching with about 14 lateral branches per plant.

*Usage.*—Appropriate for hanging baskets, window boxes, patio containers and landscape applications.

*Plant height.*—About 18 cm.

*Plant diameter.*—About 34 cm.

*Vigor.*—Vigorous.

*Lateral branches.*—Length: About 26 cm. Diameter: About 3 mm. Internode length: About 1 to 2.5 cm. Texture: Pubescent. Color: 144C.

*Foliage description.*—Arrangement: Opposite; simple. Quantity per lateral branch: About 24. Length: About 5.5 cm. Width: About 3.4 cm. Shape: Ovate to elliptic. Apex: Broadly acute. Base: Attenuate. Margin: Entire. Texture: Slightly pubescent; glandular, viscid. Venation pattern: Arcuate. Color: Young foliage, upper surface: 138A. Young foliage, lower surface: 138B. Mature foliage, upper surface: More green than 147A. Mature foliage, lower surface: 147B. Venation, upper and lower surfaces: 147D. Petiole length: About 1 cm. Petiole diameter: About 4 mm. Petiole color: 147D.

Flower description:

*Flower type and habit.*—Double flowers; flowers face mostly upward or outward; axillary. Flowers persistent. Very freely flowering, about 10 flowers and flower buds per lateral branch.

*Natural flowering season.*—Long day responsive; spring until frost in the autumn; flowering continuous.

*Flower longevity on the plant.*—About 4 days.

*Fragrance.*—Not detected.

*Flower size.*—Diameter: About 7.5 cm. Tube length: About 3 cm. Throat diameter, distal end: About 2 cm. Tube diameter, proximal end: About 7 mm.

*Flower buds* (*showing color*).—Length: About 2.3 cm. Diameter: At apex, about 1.5 cm; at base, about 6 mm. Shape: Elongated oblong with ruffled apices. Color: 84C to 84D.

*Corolla.*—Quantity/arrangement: Five fused outer petals, funnelform; interior to outer whorl, ten progressively smaller petaloids. Petal length from throat: About 3.7 cm. Petal width: About 5 cm. Petal/petaloid shape: Roughly spatulate or fan-shaped. Petal/petaloid apex: Rounded and emarginate; ruffled. Petal/petaloid margin: Entire; ruffled. Petal/petaloid texture: Smooth, velvety. Color: Petal/petaloid, upper surface, when opening: 57A. Petal/petaloid, lower surface, when opening: Ground color, 75B; central stripe, 75C. Petal/petaloid, upper surface, fully opened: Center and base, 66A; at margins, 66C; with subsequent development, margins fade to 73A to 73B. Petal/petaloid, lower surface, fully opened: 67D. Flower throat (inside): 157A; 146D at base. Flower tube (outside): 157A; 146D at base. Venation, upper petal surface: 67A. Venation, lower petal surface: 144D. Venation, throat: 60B. Venation, tube: 144C.

*Sepals.*—Arrangement/appearance: Single whorl of five sepals fused at base, star-shaped. Length: About 1 cm. Width: About 2.5 mm. Shape: Strap-like; elongate. Apex: Rounded. Margin: Entire. Texture, both surfaces: Pubescent. Color: Upper surface: 147A to 147B. Lower surface: 147B.

*Peduncles.*—Length: About 4.25 cm. Width: About 1.5 mm. Angle: About 60 to 80° from the stem. Strength: Strong. Texture: Pubescent. Color: 144A.

*Reproductive organs.*—Stamens: Quantity/type: About 7 to 8 petaloid stamens. Anther shape: Ovoid to bi-lobed. Anther length: About 2 mm. Anther color: 155A. Pollen amount: Scarce. Pollen color: 155A. Pistil: None observed.

*Seed/fruit.*—Seed nor fruit production has not been observed.

Disease/pest resistance: Plants of the new Petunia have not been noted to be resistant to pathogens or pests common to Petunia.

Temperature tolerance: Plants of the new Petunia have been observed to tolerate temperatures from 4 to 33° C.

I claim:

1. A new and distinct cultivar of Petunia plant named 'Cobdarkink', as illustrated and described.

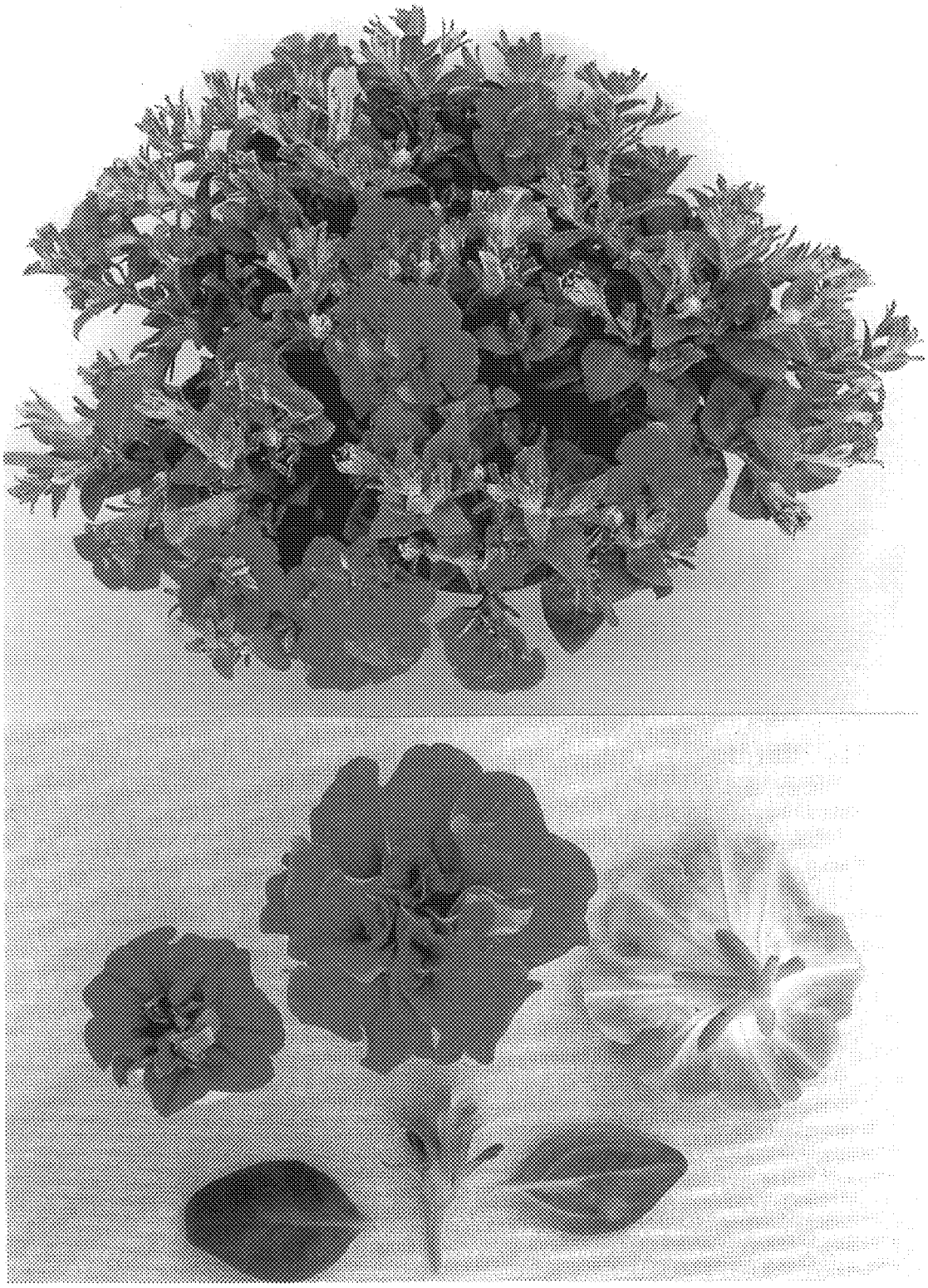

* * * * *